United States Patent [19]
Becker et al.

[11] Patent Number: 5,898,309
[45] Date of Patent: Apr. 27, 1999

[54] METHOD FOR DETERMINING SPECIFIC MATERIAL CHARACTERISTICS

[75] Inventors: Achim Becker, Darmstadt; Jan Menzel, Frankfurt, both of Germany

[73] Assignee: Filterwerk Mann & Hummel GmbH, Ludwigsburg, Germany

[21] Appl. No.: 08/725,024

[22] Filed: Oct. 2, 1996

[30] Foreign Application Priority Data

Oct. 2, 1995 [DE] Germany .................. 195 36 766

[51] Int. Cl.⁶ ........................................ G01R 27/26
[52] U.S. Cl. ........................ 324/689; 324/664; 324/695; 324/665; 361/286
[58] Field of Search .................. 73/861.73, 861.74; 324/689, 664, 665, 685, 695; 361/286

[56] References Cited

U.S. PATENT DOCUMENTS

| | | |
|---|---|---|
| Re. 28,422 | 5/1975 | MacKinney ............................ 324/695 |
| 1,826,247 | 10/1931 | Heppenstall ........................... 324/695 |
| 3,482,162 | 12/1969 | Wochnowski ........................... 374/664 |
| 4,399,100 | 8/1983 | Zsolnay et al. . |
| 4,403,191 | 9/1983 | Satake ...................................... 324/664 |
| 4,547,725 | 10/1985 | Oetiker .................................... 324/665 |
| 4,584,522 | 4/1986 | Varela . |
| 4,791,354 | 12/1988 | Wardell . |
| 4,932,243 | 6/1990 | Suh et al. . |
| 5,317,252 | 5/1994 | Kranbuehl . |

FOREIGN PATENT DOCUMENTS

| | | |
|---|---|---|
| 108629 | 5/1984 | European Pat. Off. . |
| 207377 | 1/1987 | European Pat. Off. . |

*Primary Examiner*—Josie Ballato
*Assistant Examiner*—Jose M. Solis
*Attorney, Agent, or Firm*—Evenson, McKeown, Edwards & Lenahan, P. L. L. C.

[57] ABSTRACT

A method and apparatus for determining specific material characteristics of plastic materials in which the plastic material is disposed between electrodes of a capacitive sensor and the impedance is measured and compared to a reference value, preferably stored in a computer.

9 Claims, 3 Drawing Sheets

METHOD FOR DETERMINING SPECIFIC MATERIAL CHARACTERISTICS

BACKGROUND OF THE INVENTION

This invention relates to a method for determining specific material characteristics of plastics.

A method of this type is disclosed, for example, in U.S. Pat. No. 4,568,874, which relates to the non-invasive measurement of material, for example a plastic material, with an electrical field. In the known method, three electrodes are necessary, two electrodes being configured as measuring electrodes. An additional electrode serves for shielding for the two measuring electrodes. It is also known to provide a shunt electrode instead of an electrode for shielding. With such a shunt electrode, a compensation of certain material properties is achieved. A disadvantage of the known system is, however, that the sensor technology is quite complicated and is hampered by a high uncertainty factor.

SUMMARY OF THE INVENTION

It is therefore the object of the invention to provide a method for determining specific material characteristics which will yield useful and reliable answers.

Another object of the invention is to provide a method for determining specific material characteristics which is uncomplicated in design and execution.

It is also an object of the invention to provide an apparatus for determining specific material characteristics of a material such as a plastic.

These and other objects have been achieved in accordance with the present invention by providing a method for determining a specific material characteristic of a plastic, comprising the steps of disposing the plastic between electrodes of a capacitive sensor; biasing the sensor with alternating current of at least one specific frequency; measuring the impedance, and comparing the measured value with a reference value for a specific material characteristic of the plastic.

In accordance with a further aspect of the invention, the objects also have been achieved by providing an apparatus for determining specific material characteristics of a plastic material, comprising a sensor which comprises two electrical conductors between which the material to be analyzed is situated, a system for generating the alternating-current signal, a system for evaluating capacitance or conductivity, and a system for comparing the measured value with a reference values indicative of a known material characteristic.

An important advantage of the invention is that a capacitive sensor is fed with an alternating voltage, and the impedance which can be measured directly constitutes the reference magnitude for a specific material characteristic.

In accordance with one advantageous embodiment of the invention, the impedance is determined within a specific frequency range. This means that the measurement is performed with a plurality of discrete frequencies or within a frequency spectrum. This leads to a measurement curve which permits the output of information on a material characteristic or on the ambient conditions, such as temperature for example.

In accordance with another preferred embodiment of the invention, the impedance can also be determined during a change in the temperature of the material. This temperature change results in an impedance change which can establish certain material characteristics. The temperature change may either be continuous or occur in steps.

In one preferred evaluation method according to the invention, a plurality of material characteristics can be determined from the measurement. For example, the composition of the material, its molecular state, that is, whether the material is in the crystalline or amorphous state, the dryness, that is the moisture still present in the material, and the product temperature, but also the mass transmission zone, for example in zeolites, can be learned. Furthermore, the loose bulk density or the ratio of admixture of different materials, for example the ratio of new material to recycled material, can be determined.

In one preferred embodiment of the invention, a useful apparatus for carrying out the method of the invention comprises a sensor which has essentially two electrical conductors between which the material to be analyzed is situated. An alternating current signal is fed to this sensor, and the capacitance or the impedance is measured with an instrument. The average can be compared with a given characteristic magnitude, and the material characteristic can be learned from the comparison.

In one advantageous apparatus embodiment, the sensor is constructed with at least two plates sloping toward one another. The plates are in a hopper-like arrangement. This has the advantage that the material, if it is a bulk material, has a standardized bulk density within a hopper constructed in this way. Of course, the sensor can also be constructed in other forms, such as for example two parallel plates, plates in an annular arrangement, or conductors extending parallel to each other.

These and other features of preferred embodiments of the invention, in addition to being set forth in the claims, are also disclosed in the specification and/or the drawings, and the individual features each may be implemented in embodiments of the invention either individually or in the form of subcombinations of two or more features and can be applied to other fields of use and may constitute advantageous, separately protectable constructions for which protection is also claimed.

BRIEF DESCRIPTION OF THE DRAWINGS

The invention will be described in further detail hereinafter with reference to illustrative preferred embodiments shown in the accompanying drawings, in which.

DETAILED DESCRIPTION OF PREFERRED EMBODIMENTS

Figure 1:
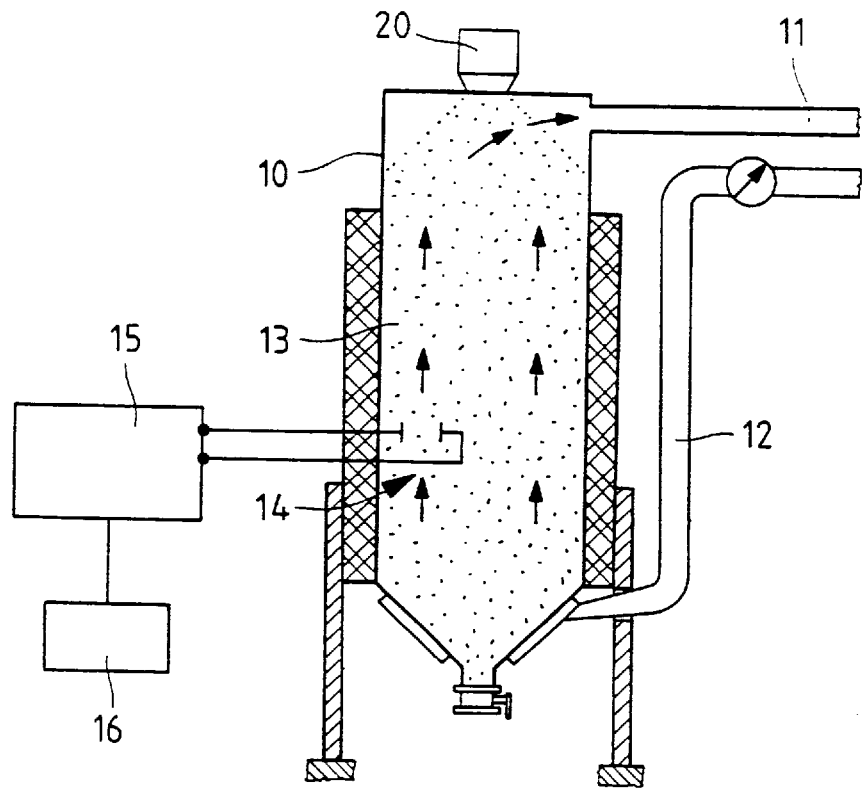
FIG. 1 is representation of a dryer for plastic granules with a system for determining material characteristics in accordance with the invention.

FIG. 1 shows a dryer for plastic granules. It comprises a tank 10 which is continuously filled with granules through a filler means 20. Dry, heated air is fed to the tank through the line 12. This air flows through the plastic granules 13 in the tank and through line 11 to an air drying system not shown in the drawing. In the tank 10 there is a sensor in the form of a plate sensor 14. This sensor is connected to an analyzer unit 15. The analyzer unit is connected to a display 16. The analyzer unit 15 supplies the sensor with an alternating current within a specific frequency spectrum or with a particular frequency. The measured capacitance is the measure for a particular material characteristic of the bulk material or plastic granules. By applying specific different electrical alternating fields to a material and measuring the electrical impedance, momentary magnitudes representing momentary data concerning the state of the material can be determined clearly. The process is based on the fact that characteristics specific to the individual components can be displayed especially well in particular alternating field ranges.

Figure 2:
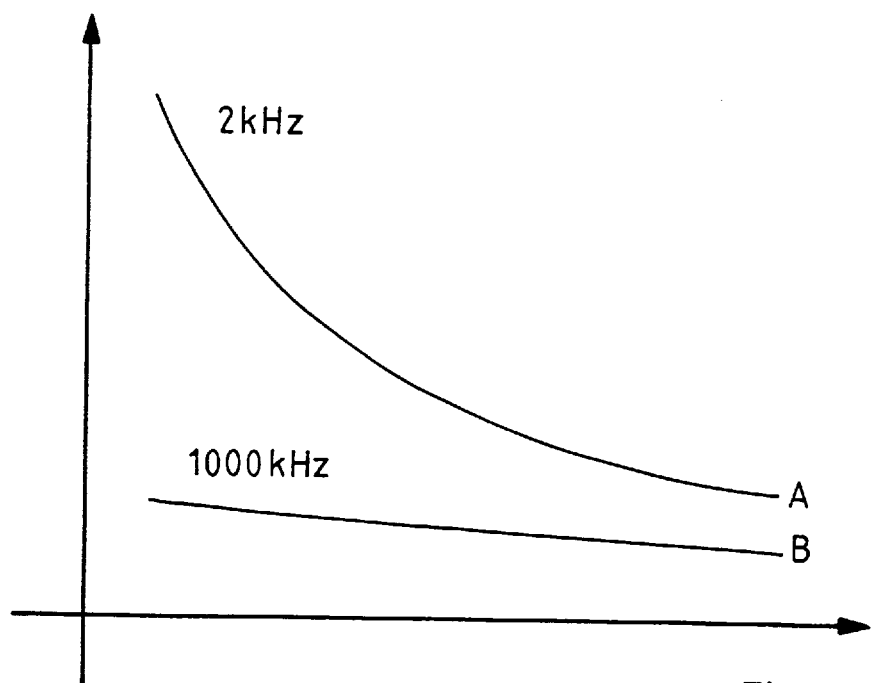
FIG. 2 is a graph illustrating how a measured signal changes with variations in temperature.

FIG. 2 shows a typical signal curve. The relation of the temperature-related characteristic of the material of the plastic granules is determined by varying the temperature of the granules and simultaneously recording the signal data. The optimum measurement frequency is selected such that any temperature change produces the greatest possible change in the signal. The measurement of the temperature is not a spot measurement. The mixed temperature of the granule elements in the sensor is measured. FIG. 2 shows that at a lesser temperature the measured signal A with a frequency of 2 kilohertz has a high level which decreases with increasing temperature. If the frequency of the measuring signal is 1000 kiloHertz, the variation over a certain temperature range is less pronounced. It is therefore advantageous to use signal A to determine the granule temperature.

The moisture content of a hygroscopic material can likewise be measured by this method. Hygroscopic material serves to absorb moisture which develops, for example, in the drying of plastic granules. The hygroscopic material takes up moisture from moist air flowing through it. A wide electrical frequency band is applied to a sensor that is situated in the material stream. A computer receives the measured data. The measuring frequency is selected such that any variation in moisture will produce the greatest possible signal change. This measuring frequency will depend on the type of material and the temperature. The material characteristic curve is stored in a computer unit and establishes the relationship between moisture content and the electrical signal. By comparing the measured value with the characteristic curve, the instantaneous moisture content can be determined.

Figure 3:
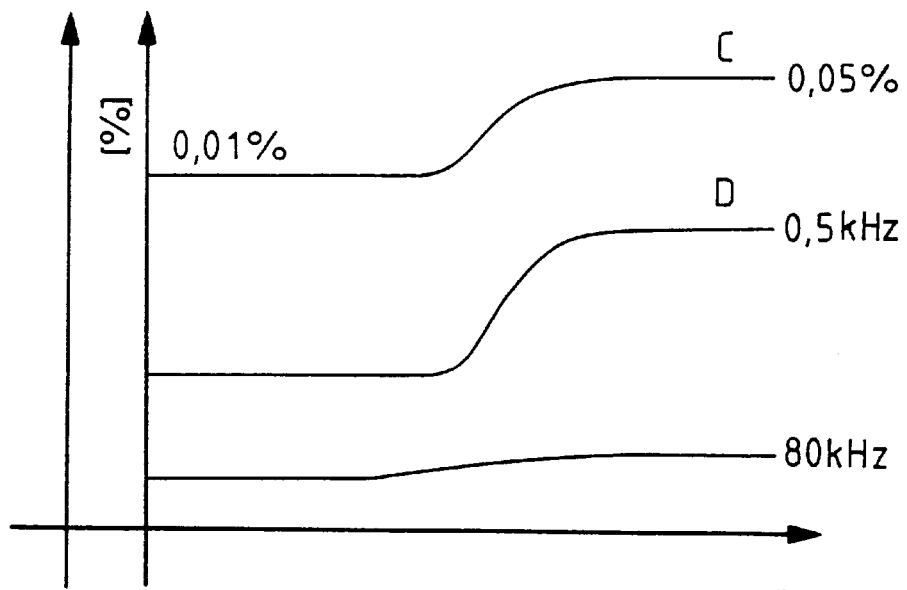
FIG. 3 is a graph illustrating how a signal changes with variations in moisture content.

The curve C in the diagram in FIG. 3 illustrates the relationship between the measuring signal and the relative humidity as the relative humidity increases from 0.01% to 0.05%. The measuring signal that was recorded at a frequency of 80 kiloHertz (curve D) shows, for the increase in relative humidity, an amplitude increase which is analogous to the increase in the relative humidity and thus is a measure of the moisture content of the hygroscopic material.

Figure 4:
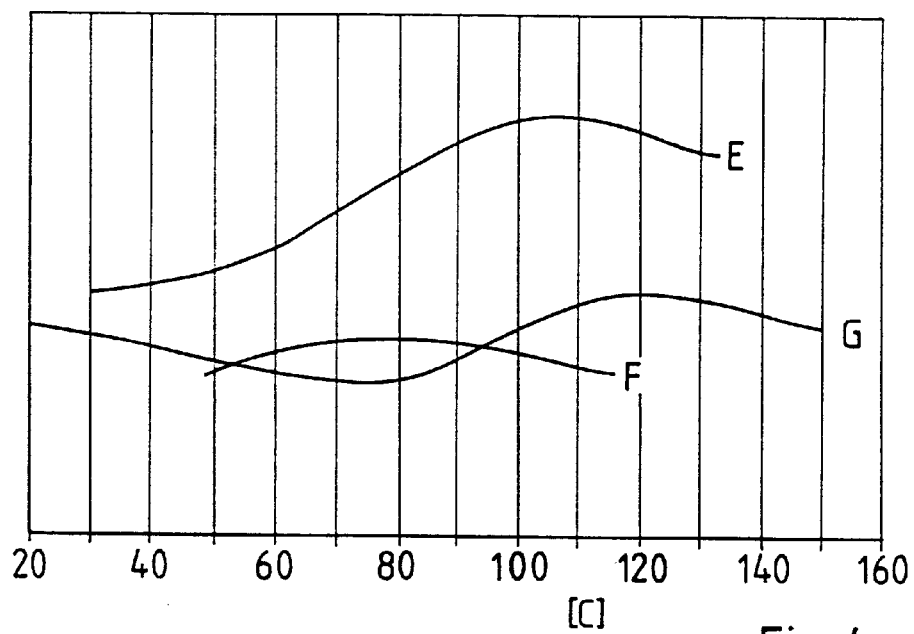
FIG. 4 is a graph depicting characteristic fingerprints of plastic granular materials.

FIG. 4 shows the curves for the measurement of different plastics in a so-called "fingerprint". These curves were recorded with a temperature variation ranging from 20 to 160° C. Curve E shows a polyamide, curve F a copolyester and curve G a polyethylene plastic. It is also possible, of course, to record different materials with certain mixture ratios as so-called "fingerprints" and to compare the sensed material with these data. The ratio of a mixture can thus be determined.

Figure 5:
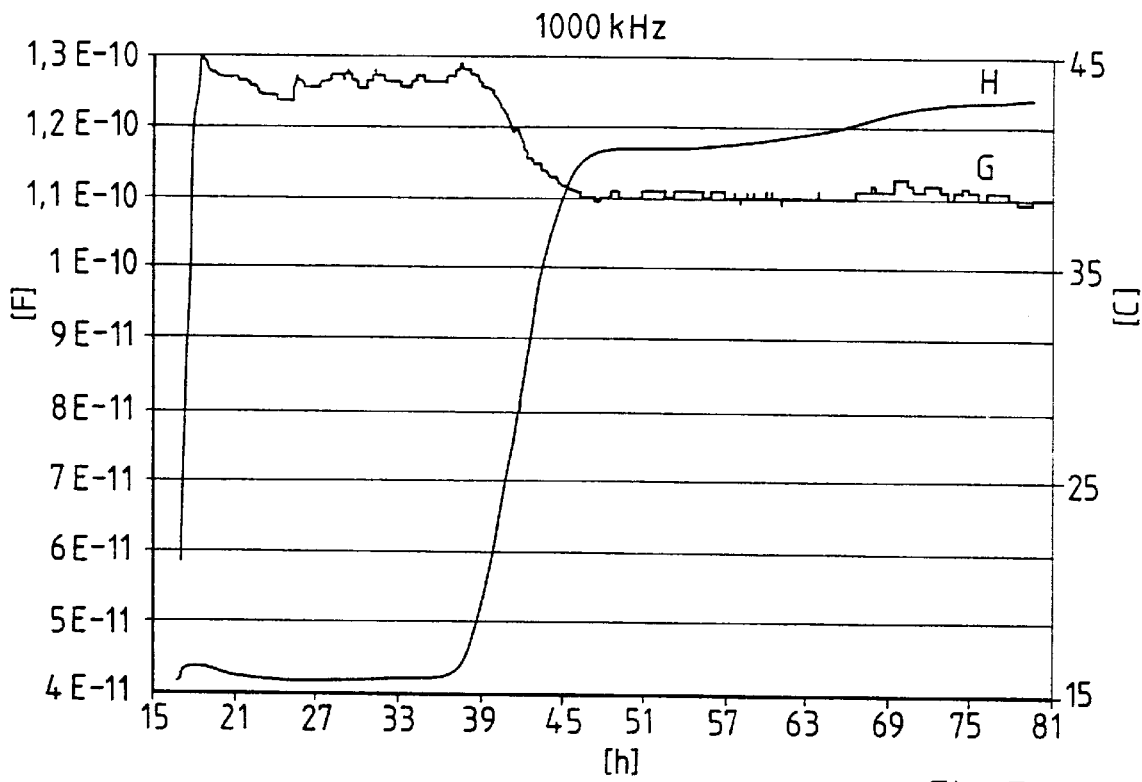
FIG. 5 is a graph depicting a signal curve with zeolite.

FIG. 5 shows the relationship between the material temperature and the capacitance signal. When the temperature (curve G) was decreased from a certain point over a period of time, the capacitance increased very greatly within this range. The capacitance is thus a signal which directly indicates the temperature being measured.

Figure 6:
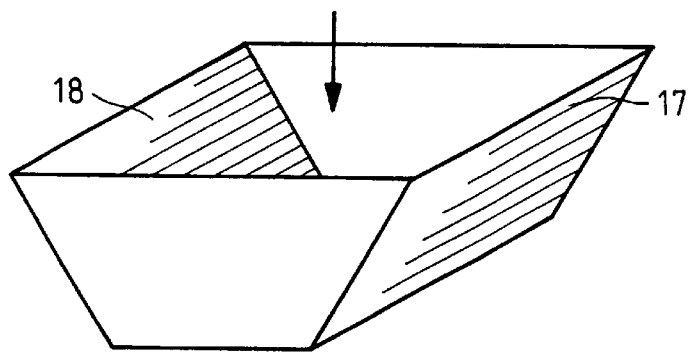
FIG. 6 is an illustration of a capacitive sensor useful in carrying out the method of the invention.

FIG. 6 shows a sensor composed of two plates 17 and 18, which slope towards one another. The plastic granulate to be sensed is passed downwardly through this sensor. Due to the size of the outlet area, which is smaller than that of the inlet area, a certain retardation of the flow of material forms, which makes it possible to gauge the bulk density of the material within the sensor.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A method for determining a specific material characteristic of a plastic, said method comprising the steps of:

providing a capacitive sensor within a material container, said sensor comprising electrodes defined by a pair of plates which are inclined relative to one another so as to define an inlet area and an outlet area which is smaller than the inlet area;

passing the plastic between said electrodes of the capacitive sensor;

biasing the sensor with alternating current of at least one specific frequency;

measuring an impedance; and comparing a measured value of the impedance with a reference value for a specific material characteristic of the plastic.

2. A method according to claim 1, wherein the impedance is measured over a specific frequency range.

3. A method according to claim 1, wherein the impedance is measured during a temperature change.

4. A method according to claim 3, wherein the temperature change is carried out continuously.

5. A method according to claim 3, wherein the temperature change is carried out in steps.

6. A method according to claim 1, wherein said specific material characteristic is any of an identity of the material, a composition of the material, a molecular state of the material, a moisture content, an average product temperature, a mass transition zone, a bulk density, and a mixture ratio of different constituents.

7. A method according to claim 1, wherein said reference value is stored electronically in a computer and said comparing step is effected electronically by said computer.

8. An apparatus for determining specific material characteristics of a plastic material, said apparatus comprising:

a sensor which comprises two electrical conductors defined within a material container by a pair of plates, said plates being inclined relative to one another so as to define an inlet area and an outlet area which is smaller than the inlet area, the material to be analyzed being situated between said plates, a system for generating an alternating-current signal, a system for evaluating capacitance or conductivity, and a system for comparing the measured value with reference values indicative of known material characteristics.

9. An apparatus according to claim 8, wherein said plates are arranged converging toward each other in a downward direction such that bulk material passed therebetween experiences flow congestion, whereby an evaluation of the bulk density of the bulk material is facilitated.

* * * * *